United States Patent
Machluf et al.

(10) Patent No.: US 10,085,946 B2
(45) Date of Patent: Oct. 2, 2018

(54) USE OF DECELLULARIZED EXTRACELLULAR MATRIX FOR ENCAPSULATING CELLS

(71) Applicant: Technion Research & Development Foundation Limited, Haifa (IL)

(72) Inventors: Marcelle Machluf, Haifa (IL); Deborah Chaimov, Carmiel (IL)

(73) Assignee: Technion Research & Development Foundation Limited, Haifa (IL)

( * ) Notice: Subject to any disclaimer, the term of this patent is extended or adjusted under 35 U.S.C. 154(b) by 0 days.

(21) Appl. No.: 14/425,737

(22) PCT Filed: Sep. 3, 2013

(86) PCT No.: PCT/IL2013/050748
§ 371 (c)(1),
(2) Date: Mar. 4, 2015

(87) PCT Pub. No.: WO2014/037942
PCT Pub. Date: Mar. 13, 2014

(65) Prior Publication Data
US 2015/0216812 A1    Aug. 6, 2015

Related U.S. Application Data

(60) Provisional application No. 61/696,368, filed on Sep. 4, 2012.

(51) Int. Cl.
*A61K 9/50* (2006.01)
*A61K 35/12* (2015.01)
*A61K 35/407* (2015.01)
*A61K 35/39* (2015.01)
*A61K 35/34* (2015.01)

(52) U.S. Cl.
CPC .......... *A61K 9/5063* (2013.01); *A61K 9/5015* (2013.01); *A61K 9/5036* (2013.01); *A61K 9/5089* (2013.01); *A61K 35/12* (2013.01); *A61K 35/39* (2013.01); *A61K 35/407* (2013.01); *A61K 35/34* (2013.01)

(58) Field of Classification Search
CPC .... A61K 9/5015; A61K 9/5036; A61K 35/12; A61K 35/34
See application file for complete search history.

(56) References Cited

U.S. PATENT DOCUMENTS

| | | |
|---|---|---|
| 5,294,446 A | 3/1994 | Schlameus et al. |
| 5,855,620 A | 1/1999 | Bishopric et al. |
| 6,179,872 B1 * | 1/2001 | Bell ............... A61L 27/24 428/304.4 |
| 6,734,018 B2 | 5/2004 | Wolfinbarger, Jr. et al. |
| 6,743,574 B1 | 6/2004 | Wolfinbarger, Jr. et al. |
| 6,933,103 B1 | 8/2005 | Klein et al. |
| 7,943,353 B2 | 5/2011 | Yu et al. |
| 2002/0094569 A1 * | 7/2002 | Yu ............... C12N 5/0012 435/325 |
| 2002/0114845 A1 | 8/2002 | DeVore et al. |
| 2003/0014126 A1 | 1/2003 | Patel et al. |
| 2004/0076657 A1 | 4/2004 | Wolfinbarger, Jr. et al. |
| 2005/0191281 A1 | 9/2005 | Ollerenshaw et al. |
| 2005/0256588 A1 | 11/2005 | Sawa et al. |
| 2010/0189760 A1 | 7/2010 | Schaffer et al. |
| 2010/0267143 A1 | 10/2010 | Park et al. |
| 2012/0156250 A1 | 6/2012 | Christman et al. |

FOREIGN PATENT DOCUMENTS

| | | |
|---|---|---|
| EP | 0977780 | 9/2004 |
| WO | WO 00/56861 | 9/2000 |
| WO | WO 2004/105734 | 12/2004 |
| WO | WO 2005/041942 | 5/2005 |
| WO | WO 2006/095342 | 9/2006 |
| WO | WO 2006/099333 | 9/2006 |
| WO | WO 2012/064606 | 5/2012 |
| WO | WO 2014/037942 | 3/2014 |

OTHER PUBLICATIONS

Mazzitelli et al., "Production and characterization of engineered alginate-based microparticles containing ECM powder for cell/tissue engineering applications", 2011, available online Oct. 13, 2010, Acta Biomaterialia, vol. 7, pp. 1050-1062.*
Turner et al., "Design and Characterization of Tissue-Specific Extracellular Matrix-Derived Microcarriers", online publication date Dec. 15, 2011, Tissue Engineering: Part C, vol. 18, No. 3, pp. 186-197.*
Supplementary European Search Report and the European Search Opinion dated Feb. 12, 2016 From the European Patent Officce Re. Application No. 13835726.4.
Turner et al. "Design and Characterization of Tissue-Specific Extracellular Matrix-Derived Microcarriers", Tissue Engineering Part C, XP009165009, 18(3): 186-197, Mar. 1, 2012. Abstract, p. 187, r-h col., Para 3-5.
International Preliminary Report on Patentability dated Mar. 19, 2015 From the International Bureau of WIPO Re. Application No. PCT/IL2013/050748.
International Search Report and the Written Opinion dated Dec. 18, 2013 From the International Searching Authority Re. Application No. PCT/IL2013/050748.
Freytes et al. "Preparation and Rheological Characterization of a Gel Form of the Porcine Urinary Bladder Matrix", Biomaterials, 29: 1630-1637, 2008.

(Continued)

*Primary Examiner* — Michael B. Pallay

(57) ABSTRACT

A microparticle for cell encapsulation is provided, having a core which comprises continuous fibers of decellularized extracellular matrix (ECM) and, optionally, an outer layer. Also provided are methods of encapsulating cells in the microparticle, pharmaceutical compositions comprising the microparticle, and methods of treating disease in animals employing the microparticles of the invention, for example, treating Diabetes.

14 Claims, 9 Drawing Sheets
(9 of 9 Drawing Sheet(s) Filed in Color)

(56) References Cited

OTHER PUBLICATIONS

Mazzitelli et al. "Production and Characterization of Engineered Alginate-Based Microparticles Containing ECM Powder for Cell/Tissue Engineering Applications", Acta Biomaterialia, 7(3): 1050-1062, Mar. 2011. Para 3.6-3.10, p. 1057-1061.
Communication Pursuant to Article 94(3) EPC dated Mar. 10, 2017 From the European Patent Office Re. Application No. 13835726.4. (4 Pages).
Communication Pursuant to Article 94(3) EPC dated Jan. 2, 2018 From the European Patent Office Re. Application No. 13835726.4. (6 Pages).
Yu et al. "The Use of Human Mesenchymal Stem Cells Encapsulated in RGD Modified Alginate Microspheres in the Repair of Myocardial Infarction in the Rat", Biomaterials, XP027124633, 31(27): 7012-70270, Published Online Jun. 20, 2010.
Office Action dated Oct. 25, 2017 From the Israel Patent Office Re. Application No. 237574 and Its Translation Into English. (9 Pages).

\* cited by examiner

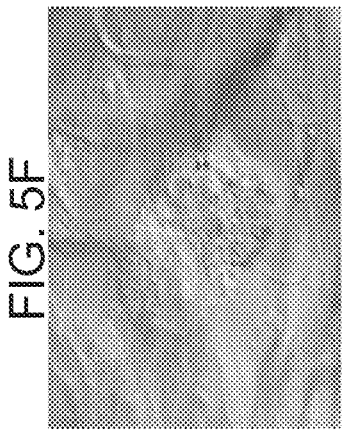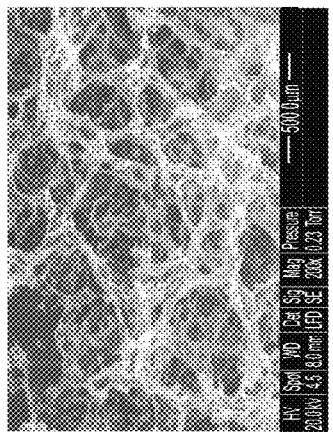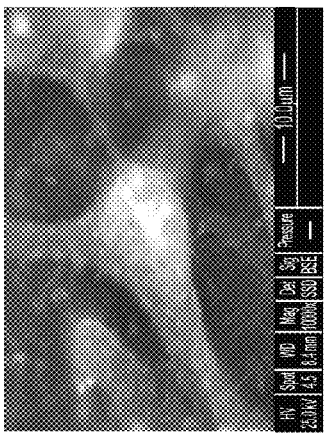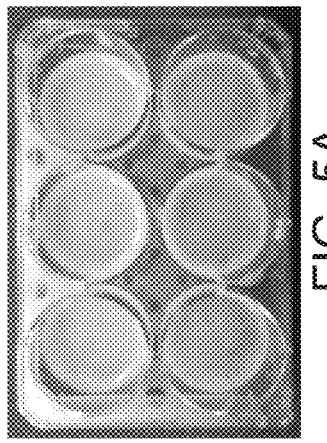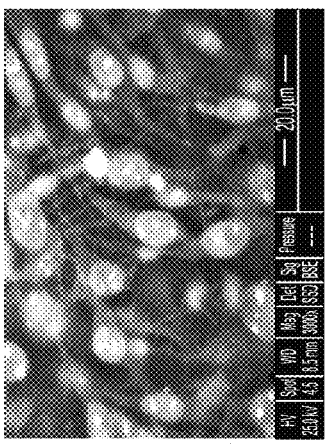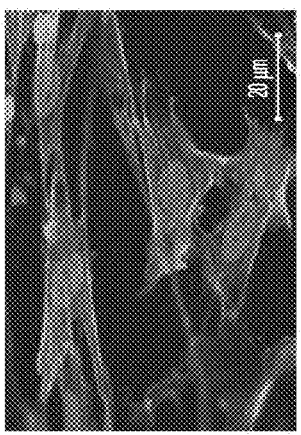

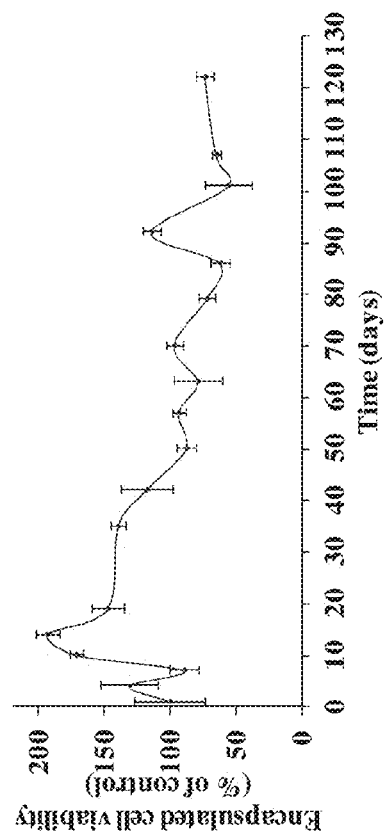
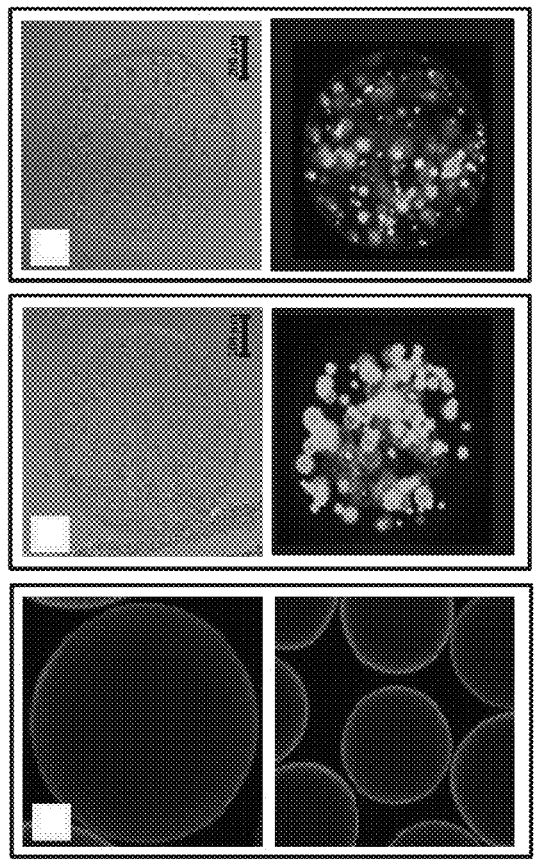
FIG. 6A
FIG. 6B
FIG. 6C
FIG. 6D

USE OF DECELLULARIZED EXTRACELLULAR MATRIX FOR ENCAPSULATING CELLS

RELATED APPLICATIONS

This application is a National Phase of PCT Patent Application No. PCT/IL2013/050748 having International filing date of Sept. 3, 2013, which claims benefit of priority under 35 USC § 119(e) of U.S. Provisional Patent Application No. 61/696,368, filed on Sept. 4, 2012. The contents of the above applications are all incorporated by reference as if fully set forth herein in their entirety.

FIELD AND BACKGROUND OF THE INVENTION

The present invention, in some embodiments thereof, relates the use of decellularized extracellular matrix for encapsulating cells.

Cell encapsulation, a strategy whereby a pool of live cells is entrapped within a semipermeable membrane, represents an evolving branch of biotechnology and regenerative medicine.

Cell capsules are intended to protect the entrapped cell/tissue fragments against the components of the host immune system, while simultaneously permitting the unhindered passage of nutrients, oxygen and secreted therapeutics factors, allowing for the controlled delivery of therapeutic products to specific physiological sites in order to restore lost function due to disease or degeneration.

Since cells are capable of secreting therapeutics such as hormones or biological proteins in response to an external stimulus they may be used as therapeutics in the treatment of a myriad of diseases including endocrine disorders (diabetes, hypoparathyroidism) central nervous system disorders (Parkinson's and Alzheimer's), as well as conditions such as heart disease, and cancer. Further, cells may be engineered so as to express useful proteins, thereby increasing the range of diseases for which they may be used as therapeutics.

Alginates are a family of unbranched anionic polysaccharides derived from brown algae (Phaeophyta) which occur extracellularly and intracellularly at approximately 20% to 40% of the dry weight. The 1,4-linked $\alpha$-1-guluronate (G) and $\beta$-d-mannuronate (M) are arranged in homopolymeric (GGG blocks and MMM blocks) or heteropolymeric block structures (MGM blocks). Cell walls of brown algae also contain 5% to 20% of fucoidan, a branched polysaccharide sulphate ester with 1-fucose four-sulfate blocks as the major component. Commercial alginates are often extracted from algae washed ashore, and their properties depend on the harvesting and extraction processes.

Alginate has been employed for encapsulating cells to be transplanted, since it is biocompatible both with host and with enclosed cells; moreover, its quality can be constantly ensured. Furthermore, the use of alginate ensures that the surface of the capsules is not rough thereby preventing the elicitation of immunological reactions when implanted.

Decellularized extracellular cell matrix (which comprises molecules such as the collagen family (as a major macromolecule), elastic fibers, glycosoaminoglycans (GAG) and proteoglycans, and adhesive glycoproteins) has also been proposed to fabricate capsules for cell encapsulation. The decellularized extracellular cell matrix serves as a network supporting the attachment and proliferation of cells.

Generation of decellularized ECM from natural tissues involves subjecting the tissues to enzymatic cellular digestion (e.g., using trypsin), hypotonic, hypertonic and/or low ionic strength buffers, detergent and chemical digestion (e.g., using SDS, Triton-X-100, ammonium hydroxide, peracetic acid) and non-micellar amphipatic molecules such as polyethylene glycole (PEG) (See for example, U.S. Pat. Appl. Nos. 20040076657, 20030014126, 20020114845, 20050191281, 20050256588 and U.S. Pat. Nos. 6,933,103, 6,743,574, 6,734,018, 5,855,620; and WO2006/095342 which are fully incorporated herein by reference).

Freytes et al., Biomaterials 29 (2008) 1630-1637 teaches a method of generating soluble, decellularized ECM and preparation of gels therefrom.

U.S. Patent Application No. 20120156250 teaches soluble decellularized ECM.

U.S. Patent Application No. 201000267143 teaches a scaffold of decellularized extracellular matrix and alginate.

U.S. Patent Application Nos. 20100189760 and 20100172942 teach a multilayered capsule for cell encapsulation, wherein at least one of the layers comprises alginate.

Mazzitelli et al., Acta Biomaterialia 7 (2011) 1050-1062 teaches cell encapsulating particles comprising decellularized ECM and alginate.

SUMMARY OF THE INVENTION

According to an aspect of some embodiments of the present invention there is provided a microparticle for cell encapsulation, having a core which comprises continuous fibers of decellularized extracellular matrix (ECM).

According to an aspect of some embodiments of the present invention there is provided a microparticle for cell encapsulation, having a core which comprises continuous fibers of decellularized extracellular matrix (ECM) and an outer layer comprising a polymerizing agent, wherein an amount of polymerizing agent in the outer layer is at least 10 times the amount of polymerizing agent in the core.

According to an aspect of some embodiments of the present invention there is provided a microparticle for cell encapsulation having a core which comprises continuous fibers of decellularized extracellular matrix (ECM) and an outer layer comprising a polyion.

According to an aspect of some embodiments of the present invention there is provided a method of encapsulating a cell comprising:

(a) contacting solubilized decellularized ECM and cells in the presence of a polymerizing agent to generate a mixture;

(b) generating microparticles comprising the cells; and (c) depolymerization the polymerizing agent, thereby encapsulating the cell.

According to an aspect of some embodiments of the present invention there is provided a method of treating a medical condition which may benefit from cell transplantation in a subject in need thereof, comprising administering to the subject a therapeutically effective amount of a plurality of the microparticles provided herein, thereby treating the medical condition.

According to an aspect of some embodiments of the present invention there is provided a pharmaceutical composition comprising the microparticles provided herein as the active agent and a pharmaceutically acceptable carrier.

According to an aspect of some embodiments of the present invention there is provided a method of treating Diabetes in a subject in need thereof, comprising administering to the subject a therapeutically effective amount of a plurality of the microparticle described herein, thereby treating Diabetes.

According to some embodiments of the invention, the outer layer further comprises a polyion.

According to some embodiments of the invention, the microparticle has an outer layer which encapsulates the core, the outer layer comprising a polyion.

According to some embodiments of the invention, the polyion is selected from the group consisting of poly-L-lysine, poly-D-lysine, poly-L,D-lysine, poly-L-omithine, poly-D-omithine, poly-L,D ornithine, chitosan, polyacrylamide, poly(vinyl alcohol), chitosan and combinations thereof.

According to some embodiments of the invention, the outer layer further comprises a polymerizing agent.

According to some embodiments of the invention, the polymerizing agent is selected from the group consisting of chitosan, polymethacrylic acid, a polysaccharide, poly (ethylene glycol) (PEG) and poly (hydroxyethyl) methacrylate (HEMA).

According to some embodiments of the invention, the polysaccharide is selected from the group consisting of alginate, hyaluronic acid and agarose.

According to some embodiments of the invention, the core is substantially devoid of the polymerizing agent.

According to some embodiments of the invention, the amount of the polymerizing agent in the outer layer is at least ten times greater than an amount of the polymerizing agent in the core.

According to some embodiments of the invention, the thickness of the outer layer is between about 10 μm to 30 μm.

According to some embodiments of the invention, the microparticle further comprises a plurality of cells.

According to some embodiments of the invention, the microparticle is between 300-1000 μm in diameter.

According to some embodiments of the invention, the polymerizing agent is selected from the group consisting of chitosan, polymethacrylic acid, a polysaccharide, poly (ethylene glycol) (PEG) and poly (hydroxyethyl) methacrylate (HEMA).

According to some embodiments of the invention, the polysaccharide is selected from the group consisting of alginate, hyaluronic acid and agarose.

According to some embodiments of the invention, the polysaccharide is alginate.

According to some embodiments of the invention, the depolymerizing is effected by contacting the microparticles with a chelating agent.

According to some embodiments of the invention, the chelating agent comprises calcium citrate or sodium citrate.

According to some embodiments of the invention, the method further comprises contacting the microparticles following step (b) and prior to step (c) with a polyion to generate coated microparticles.

According to some embodiments of the invention, the polyion is selected from the group consisting of poly-L-lysine, poly-D-lysine, poly-L,D-lysine, poly-L-omithine, poly-D-omithine, poly-L,D ornithine, chitosan, polyacrylamide, poly(vinyl alcohol), chitosan and combinations thereof.

According to some embodiments of the invention, generating the microparticles is effected by extruding the mixture into a crosslinking solution.

According to some embodiments of the invention, the crosslinking solution comprises calcium chloride or a strontium solution.

According to some embodiments of the invention, the decellularized extracellular matrix is derived from pancreatic tissue.

According to some embodiments of the invention, the decellularized extracellular matrix is derived from cardiac tissue.

According to some embodiments of the invention, the microparticle further comprises cells which express pancreatic beta cell markers.

According to some embodiments of the invention, the microparticle further comprises cells which express cardiac markers.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this paten or patent application publication with color drawings(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a pictorial representation of the overall process of preparation of capsules of ECM according to embodiments of the present invention.

FIG. 2 is a pictorial representation of the process of liquification and ejection of the alginate from the ECM-cell capsules coated with a PLL membrane.

FIGS. 3A-F are photographs illustrating the characterization of the decellularized pancreatic ECM. (A) Native porcine pancreas. (B) Decellularization of native porcine pancreas. (C) Sections of decellularized pancreas were stained with H&E staining in order to assure that all cellular components which can provoke immune response are removed. As seen, no traces or residues of cellular or nuclear components could be detected in the decellularized pancreas. (D) HR-SEM image exhibited typical morphology of collagen fibers. (E) Lyophilized ECM. (F) Soluble ECM.

Figures 4A, 4B:
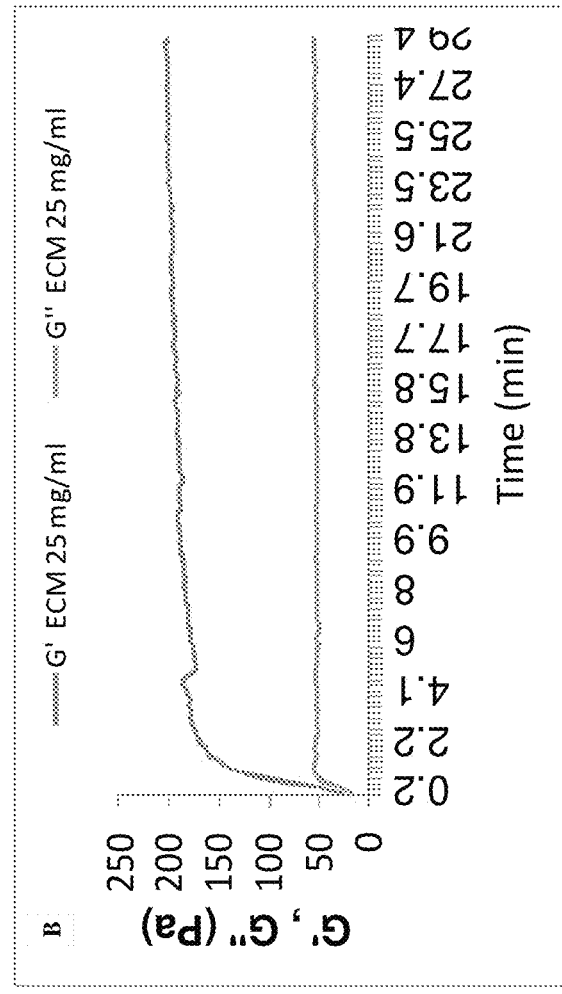

FIGS. 4A-B illustrate proteomic and rheological analysis of pancreatic ECM gel. (A) A proteomic analysis of the ECM was performed and compared to one performed on native pancreas and solubilized decellularized pancreatic matrix. Samples were digested with trypsin, analyzed by LC-MS/Mson LTQ-Orbitrap (Thermo) and identified by Mascot and Segues software against the mammalian part of the NCBI-nr database, and a decoy data base (in order to determine the false discovery rate). The same main proteins were detected in the decellularized pancreatic ECM and solubilized decellularized pancreatic matrix. Thus, it can be deduced that the acellularization process of the pancreatic ECM does not damage those proteins. Collagen 1 was significantly present in all samples. (B) Representative curve of the gelation kinetics of pancreatic gels determined during the mechanical testing of the gels based on the storage modulus (G') and the loss modulus (G").

FIGS. 5A-K illustrate the characterization and therapeutic efficacy of cells seeded on ECM gels. (A-C) 3D structure (SEM) of reconstituted liquefied ECM with (D-F) viable cells on it (WETSEM). Confocal imaging of (G) cells seeded on plate and (H) cells stained with Hoechst, phalloidin and (I) DIL. Secretion of C-peptide from (J) hMSC and (K) Hum Hep seeded on tissue culture plate (TCP) or gel, 5 days post viral transduction (***p<0.001). n=7.

FIGS. 6A-D illustrate characterization of Alginate-PLL microcapsules. (A) Encapsulated cells viability was determined using the Alamar Blue assay. It was found that both kinds of cells, Hum Hep cells and hMSC, were viable for more than 120 days. (B) Fluorescent micrographs of alginate-PLL FITC capsules and (C) encapsulated cells stained with Fluorescein Diacetate (FDA) cell viability assay were taken on day 10 and (D) 108 post encapsulation.

FIGS. 7A-G illustrate characterization and therapeutic efficacy of encapsulated cells. Encapsulated cells were stained with (A) Hoechst and (B) FDA. (C) Collagen fibers were stained with Tamra (red). (D) Double staining with Tamra+FDA (orange). Secretion of C-peptide from (E) Hum Hep cells and (F,G) hMSC 5 days post viral transduction (p<0.01, *p<0.001). n=7.

DESCRIPTION OF SPECIFIC EMBODIMENTS OF THE INVENTION

The present invention, in some embodiments thereof, relates to the use of decellularized extracellular matrix for encapsulating cells.

Encapsulating cells in hydrogels has shown promising results for reducing the immune response, but many preclinical and clinical trials results have been inconsistent because of the limited ability of hydrogels to support cellular viability and function over an extended time period. Therefore, few successful products have been fully commercialized based on these cell-encapsulation technologies. Mixing cells and polymer solutions during a cell encapsulation process generally leads to a significant decrease in cell viability, because high shear stresses can disrupt cell-cell contacts.

The present inventors have now conceived a way to protect cells during the encapsulation process by mixing them with solubilized decellularized extracellular matrix. In order to ensure that smooth capsules are generated, a polymerizing agent such as alginate is used during the encapsulation process. The polymerizing agent may subsequently be removed from the inner core of the capsules by subsequent depolymerization.

Thus, according to one aspect of the present invention, a method of encapsulating a cell is provided. The method comprises:

(a) contacting solubilized decellularized extracellular matrix (ECM) and cells in the presence of a polymerizing agent to generate a mixture;

(b) extruding the mixture into a crosslinking solution to generate microparticles comprising the cells;

(c) contacting the microparticles with a chelating agent under conditions which allow depolymerization of the polymerizing agent, thereby encapsulating the cell.

As used herein the phrase "decellularized ECM of a tissue" refers to the extracellular matrix which supports tissue organization (e.g., a natural tissue) and underwent a decellularization process (i.e., a removal of all cells from the tissue) and is thus completely devoid of any cellular components.

The phrase "completely devoid of any cellular components" as used herein refers to being more than 90%, 91%, 92%, 93%, 94%, 95%, 96%, 97%, 98%, 99%, (e.g., 100%) devoid of the cellular components present in the natural (e.g., native) tissue. As used herein, the phrase "cellular components" refers to cell membrane components or intracellular components which make up the cell. Examples of cell components include cell structures (e.g., organelles) or molecules comprised in same. Examples of such include, but are not limited to, cell nuclei, nucleic acids, residual nucleic acids (e.g., fragmented nucleic acid sequences), cell membranes and/or residual cell membranes (e.g., fragmented membranes) which are present in cells of the tissue. It will be appreciated that due to the removal of all cellular components from the tissue, such a decellularized matrix cannot induce an immunological response when implanted in a subject.

The phrase "extracellular matrix (ECM)" as used herein, refers to a complex network of materials produced and secreted by the cells of the tissue into the surrounding extracellular space and/or medium and which typically together with the cells of the tissue impart the tissue its mechanical and structural properties. Generally, the ECM includes fibrous elements (particularly collagen, elastin, or reticulin), cell adhesion polypeptides (e.g., fibronectin, laminin and adhesive glycoproteins), and space-filling molecules [usually glycosaminoglycans (GAG), proteoglycans].

A tissue-of-interest (e.g., pancreas, myocardium) may be derived from an autologous or non-autologous tissue (e.g., allogeneic or even xenogeneic tissue, due to non-immunogenicity of the resultant decellularized matrix). The tissue is removed from the subject [e.g., an animal, preferably a mammal, such as a pig, monkey or chimpanzee, or alternatively, a deceased human being (shortly after death)] and washed e.g. in a sterile saline solution (0.9% NaCl, pH=7.4) or phosphate buffered saline (PBS), which can be supplemented with antibiotics such as Penicillin/Streptomycin 250 units/ml. Although whole tissues can be used, for several applications segments of tissues may be cut e.g. sliced. Such tissue segments can be of various dimensions, depending on the original tissue used and the desired application.

To remove the vasculature surrounding and feeding the tissue, the tissue may be washed at room temperature by agitation in large amounts (e.g., 50 ml per each gram of tissue segment) of EDTA solution (0.5-10 mM, pH-7.4).

Next, the tissue is subjected to a hypertonic or hypotonic buffer to thereby obtain increased intercellular space within the tissue.

The hypertonic buffer used by the present invention can be any buffer or solution with a concentration of solutes that is higher than that present in the cytoplasm and/or the intercellular liquid within the tissue [e.g., a concentration of NaCl which is higher than 0.9% (w/v)]. Due to osmosis, incubation of the tissue with the hypertonic buffer results in increased intercellular space within the tissue.

According to another embodiment, peracetic acid is used to decellularize the tissue.

Preferably, the hypertonic buffer used by the method according to this aspect of the present invention includes sodium chloride (NaCl) at a concentration which is higher than 0.9% (w/v), preferably, higher than 1% (w/v), preferably, in the range of 1-1.2% (w/v), e.g., 1.1% (w/v).

Preferably, the hypotonic buffer used by the method according to this aspect of the present invention includes sodium chloride (NaCl) at a concentration which is lower than 0.9% (w/v), lower than 0.8% (w/v), lower than 0.7% (w/v), preferably, in the range of 0.6-0.9% (w/v), e.g., 0.7% (w/v).

According to this aspect of the present invention, the tissue is subjected to the hypertonic or hypotonic buffer for a time period leading to the biological effect, i.e., cell shrinkage which leads to increased intercellular space within the tissue.

According to a particular embodiment, the tissue is contacted with a hypertonic buffer (e.g. 1.1% w/v) and subsequently contacted with a hypotonic buffer (e.g. 0.7% w/v). This procedure may be repeated for two or more cycles.

Preferably, the hypotonic buffer used by the method according to this aspect of the present invention includes sodium chloride (NaCl) at a concentration which is lower than 0.9% (w/v), lower than 0.8% (w/v), lower than 0.7% (w/v), preferably, in the range of 0.6-0.9% (w/v), e.g., 0.7% (w/v).

Following incubation with the hypertonic/hypotonic buffer, the tissue is further subjected to an enzymatic proteolytic digestion which digests all cellular components within the tissue yet preserves the ECM components (e.g., collagen and elastin) and thus results in a matrix which exhibits the mechanical and structural properties of the original tissue ECM. It will be appreciated that measures are taken to preserve the ECM components while digesting the cellular components of the tissue. These measures are further described hereinbelow and include, for example, adjusting the concentration of the active ingredient (e.g., trypsin) within the digestion solution as well as the incubation time.

Proteolytic digestion according to this aspect of the present invention can be effected using a variety of proteolytic enzymes. Non-limiting examples of suitable proteolytic enzymes include trypsin and pancreatin which are available from various sources such as from Sigma (St Louis, Mo., USA). According to one preferred embodiment of this aspect of the present invention, proteolytic digestion is effected using trypsin.

Digestion with trypsin is preferably effected at a trypsin concentration ranging from 0.01-0.25% (w/v), more preferably, 0.02-0.2% (w/v), more preferably, 0.05-0.1 (w/v), even more preferably, a trypsin concentration of about 0.05% (w/v). For example, a trypsin solution containing 0.05% trypsin (w/v; Sigma), 0.02% EDTA (w/v) and antibiotics (Penicillin/Streptomycin 250 units/ml), pH=7.2] may be used to efficiently digest all cellular components of the tissue.

It will be appreciated that for efficient digestion of all cellular components of the tissue, each of the tissue segments may be placed in a separate vessel containing the digestion solution (e.g., a trypsin solution as described hereinabove) in a ratio of 40 ml digestion solution per each gram of tissue. Preferably, while in the digestion solution, the tissue segments are slowly agitated (e.g., at about 150 rpm) to enable complete penetration of the digestion solution to all cells of the tissue.

It should be noted that the concentration of the digestion solution and the incubation time therein depend on the type of tissue being treated and the size of tissue segments utilized and those of skilled in the art are capable of adjusting the conditions according to the desired size and type of tissue.

Preferably, the tissue segments are incubated for at least about 20 hours, more preferably, at least about 24 hours. Preferably, the digestion solution is replaced at least once such that the overall incubation time in the digestion solution is at least 40-48 hours.

Next, the cellular components are removed from the tissue. Removal of the digested components from the tissue can be effected using various wash solutions, such as detergent solutions (e.g., ionic and non ionic detergents such as SDS Triton X-100, Tween-20, Tween-80) which can be obtained from e.g., Sigma (St Louis, Mo., USA) or Biolab (Atarot, Israel, Merck Germany).

Preferably, the detergent solution used by the method according to this aspect of the present invention includes TRITON-X-100 (available from Merck). For efficient removal of all digested cellular components, TRITON-X-100 is provided at a concentration range of 0.05-2.5% (v/v), more preferably, at 0.05-2% (v/v), more preferably at 0.1-2% (v/v), even more preferably at a concentration of 1% (v/v).

Preferably, for optimized results, the detergent solution includes also ammonium hydroxide, which together with the TRITON-X-100, assists in breaking and dissolving cell nuclei, skeletal proteins, and membranes.

Preferably, ammonium hydroxide is provided at a concentration of 0.05-1.5% (v/v), more preferably, at a concentration of 0.05-1% (v/v), even more preferably, at a concentration of 0.1-1% (v/v) (e.g., 0.1%).

The concentrations of TRITON-X-100 and ammonium hydroxide in the detergent solution may vary, depending on the type and size of tissue being treated and those of skills in the art are capable of adjusting such concentration according to the tissue used.

Incubation of the tissue (or tissue segments) with the detergent solution can last from a few minutes to hours to even several days, depending on the type and size of tissue and the concentration of the detergent solution used and those of skills in the art are capable of adjusting such incubation periods. Preferably, incubation with the detergent solution is effected for at least 24-72 hours. According to one embodiment, 2-4 cycles of incubation with the detergent solution are performed until no foam is observed, such that the total incubation time may be between about 150-200 hours.

Although as described hereinabove, incubation with the detergent solution enables the removal of cell nuclei, proteins and membrane, the method according to this aspect of the present invention optionally and preferably includes an additional step of removing nucleic acids (as well as residual nucleic acids) from the tissue to thereby obtain a nucleic acid—free tissue. As used herein the phrase "nucleic acid—free tissue" refers to a tissue being more than 99% free of any nucleic acid or fragments thereof as determined using conventional methods (e.g., spectrophotometry, electrophoresis essentially as described in Example 1 of the Examples section which follows). Such a step utilizes a DNase solution (and optionally also an RNase solution). Suitable nucleases include DNase and/or RNase [Sigma, Bet Haemek Israel, 20 µg/ml in Hank balance salt solution (HBSS)].

The above described detergent solution is preferably removed by subjecting the matrix to several washes in water or saline (e.g., at least 10 washes of 30 minutes each, and 2-3 washes of 24 hours each), until there is no evident of detergent solution in the matrix.

Optionally, the decellularized ECM is then sterilized. Sterilization of the decellularized ECM may be effected using methods known in the art (e.g. 70% ethanol).

Solubilization of the decellularized ECM may be effected as described in Freytes et al., Biomaterials 29 (2008) 1630-1637 and U.S. Patent Application No. 20120156250, the contents of which are incorporated herein by reference.

Typically, in order to carry out solubilization of the decellularized ECM it is first lyophilized.

The lyophilized decellularized is typically cut into small pieces, e.g. crumbled and then subjected to a second round of proteolytic digestion. The digestion is effected under conditions that allow the proteolytic enzyme to digest and solubilize the ECM. Thus, according to one embodiment, the digestion is carried out in the presence of an acid (e.g. HCL) so as to obtain a pH of about 3-4.

Proteolytic digestion according to this aspect of the present invention can be effected using a variety of proteolytic enzymes. Non-limiting examples of suitable proteolytic enzymes include trypsin, pepsin, collaganease and pancreatin which are available from various sources such as from Sigma (St Louis, Mo., USA) and combinations thereof. Matrix degrading enzymes such as matrix metalloproteinases are also contemplated.

It should be noted that the concentration of the digestion solution and the incubation time therein depend on the type of tissue being treated and the size of tissue segments utilized and those of skilled in the art are capable of adjusting the conditions according to the desired size and type of tissue.

Preferably, the tissue segments are incubated for at least about 20 hours, more preferably, at least about 24 hours. Preferably, the digestion solution is replaced at least once such that the overall incubation time in the digestion solution is at least 40-48 hours.

Once the decellularized ECM is solubilized, the pH of the solution is increased so as to irreversibly inactivate the proteolytic enzyme (e.g. to about pH 7). The decellularized ECM may be stored at this stage at temperatures lower than 20° C.—for example 4° C. so that the decellularized ECM remains in solution.

As mentioned, the solubilized decellularized extracellular matrix (ECM) is contacted with a polymerizing agent to generate a mixture for generating capsules.

The polymerizing agent of this aspect of the present invention is preferably water soluble and may include polymers such as chitosan and polymethacrylic acid or hydrogels composed of polysaccharides (such as alginate, hyaluronic acid and agarose) or other polymers such as poly ethylene glycol, (PEG), and poly hydroxyethyl methacrylate (HEMA)).

According to a particular embodiment, the polymerizing agent is chitosan or alginate.

According to another embodiment, the polymerizing agent is alginate. Alginate is commercially available from a variety of sources—e.g. Novamatrix, Norway. The alginate may be of a viscosity less than 20 up until greater than 200 mPa·s with different G/M content (e.g. from less than 1 to greater than 1.5).

Typical ratios of volumes of polymerizing agent: decellularized ECM which are mixed to generate the mixture are between 50:50-70:30.

Cells are added to the above described mixture. Thus, for example for a 2 ml mixture, about two million cells may be added.

The present invention contemplates encapsulating any type of cell, including for example primary cells, cultured cells, single cell suspensions of cells, clusters of cells e.g. islets, cells which are comprised in tissues and/or organs etc.

The cells may be derived from any organism including for example mammalian cells, (e.g. human), plant cells, algae cells, fungal cells (e.g. yeast cells), prokaryotic cells (e.g. bacterial cells).

According to a particular embodiment the cells comprise stem cells—e.g. adult stem cells such as mesenchymal stem cells or pluripotent stem cells such as embryonic stem cells or induced pluripotent stem cells. The stem cells may be modified so as to undergo ex vivo differentiation.

According to a particular embodiment, the cells are preferably intact (i.e. whole), and preferably viable, although it will be appreciated that pre-treatment of cells, such as generation of cell extracts or non-intact cells are also contemplated by the present invention.

The cells may be fresh, frozen or preserved in any other way known in the art (e.g. cryopreserved).

According to another embodiment, the cells are derived from the pancreas or the liver.

The tissue from which the decellularized extracellular matrix is produced may be selected (i.e. matched) according to the cells which are incorporated therein.

Thus, for example when the cells are derived from the pancreas—e.g. pancreatic beta cells (or modified so as to imitate pancreatic beta cells), according to certain embodiments, the tissue from which the decellularized extracellular matrix is produced is pancreatic tissue.

In a similar fashion, when the cells are derived from cardiac tissue—e.g. cardiac myocardial cells (or modified so as to imitate cardiac myocardial cells), according to certain embodiments, the tissue from which the decellularized extracellular matrix is produced is cardiac myocardial tissue.

Typically, the cells secrete a factor (e.g. a polypeptide) that is useful for the treatment of a disease.

Such factors include for example, hormones including but not limited to insulin, thyroxine, growth hormone, testosterone, oestrogen, erythropoietin and aldosterone; enzymes, including but not limited to lysosomal enzyme such as glucocerebrosidase (GCD), acid sphingomyelinase, hexosaminidase, α-N-acetylgalactosaminidise, acid lipase, α-galactosidase, α-L-iduronidase, iduronate sulfatase, α-mannosidase, sialidase, α fucosidase, $G_{M1}$-β-galactosidase, ceramide lactosidase, arylsulfatase A, β galactosidase and ceramidase; clotting factors such as factor VIII.

According to a preferred embodiment, the cells secrete insulin.

As used herein, the term "insulin" refers to an insulin obtained by synthesis or recombination, in which the peptide sequence is the sequence of human insulin, includes the allelic variations and the homologs. The polypeptide sequence of the insulin may be modified to improve the function of the insulin (e.g. long lasting).

Cells which secrete neurotrophic factors are also contemplated by the present invention.

As used herein, the phrase "neurotrophic factor" refers to a cell factor that acts on the cerebral nervous system comprising growth, differentiation, functional maintenance and/or survival effects on neurons. Examples of neurotrophic factors include, but are not limited to, glial derived neurotrophic factor (GDNF), GenBank accession nos. L19063, L15306; brain-derived neurotrophic factor (BDNF), GenBank accession no CAA62632; neurotrophin-3 (NT-3), GenBank Accession No. M37763; neurotrophin-4/5; Neurturin (NTN), GenBank Accession No. NP_004549; Neurotrophin-4, GenBank Accession No. M86528; Persephin, GenBank accession No. AAC39640;

brain derived neurotrophic factor, (BDNF), GenBank accession No. CAA42761; artemin (ART), GenBank accession No. AAD13110; ciliary neurotrophic factor (CNTF), GenBank accession No. NP_000605; insulin growth factor-I (IGF-1), GenBank accession No. NP_000609; and Neublastin GenBank accession No. AAD21075.

Cells which secrete neuropeptides are also contemplated by the present invention. Examples of neuropeptides include, but are not limited to Oxytocin, Vasopressin, Corticotropin releasing hormone (CRH), Growth hormone releasing hormone (GHRH), Luteinizing hormone releasing hormone (LHRH), Somatostatin growth hormone release inhibiting hormone, Thyrotropin releasing hormone (TRH), Neurokinin α (substance K), Neurokinin β, Neuropeptide K, Substance P, β-endorphin, Dynorphin, Met- and leu-enkephalin, Neuropeptide tyrosine (NPY), Pancreatic polypeptide, Peptide tyrosine-tyrosine (PYY), Glucogen-like peptide-1 (GLP-1), Peptide histidine isoleucine (PHI), Pituitary adenylate cyclase activating peptide (PACAP), Vasoactive intestinal polypeptide (VIP), Brain natriuretic peptide, Calcitonin gene-related peptide (CGRP) (α- and β-form), Cholecystokinin (CCK), Galanin, Islet amyloid polypeptide (IAPP), Melanin concentrating hormone (MCH), ACTH, α-MSH, Neuropeptide FF, Neurotensin, Parathyroid hormone related protein, Agouti gene-related protein (AGRP), Cocaine and amphetamine regulated transcript (CART)/peptide, Endomorphin-1 and -2,5-HT-moduline, Hypocretins/orexins Nociceptin/orphanin FQ, Nocistatin, Prolactin releasing peptide, Secretoneurin and Urocortin.

Cells which secrete neurotransmitters are also contemplated by the present invention.

A neurotransmitter according to the teaching of the present invention can be any substances which is released on excitation from the axon terminal of a presynaptic neuron of the central or peripheral nervous system and travel across the synaptic cleft to either excite or inhibit the target cell. The neurotransmitter can be, for example, dopamine, norepinephrine, epinephrine, gamma aminobutyric acid, serotonin, acetylcholine, glycine, histamine, vasopressin, oxytocin, a tachykinin, cholecytokinin (CCK), neuropeptide Y (NPY), neurotensin, somatostatin, an opioid peptide, a purine or glutamic acid.

According to one embodiment, the cells are naïve (non-genetically modified).

The present invention also contemplates use of cells which have been genetically modified to express a recombinant protein. The recombinant protein may be a therapeutic protein or may promote in vivo longevity (AM, adrenomedullin, Jun-Ichiro et al. Tissue Eng. 2006) or may promote neurotransmitter release (e.g., such as by transfecting with tyrosine hydroxylase).

Examples of therapeutic, recombinant proteins that may be expressed in the cells of the present invention include, but are not limited to an antibody, insulin, human growth hormone (rHGH), follicle stimulating hormone, factor VIII, erythropoietin, Granulocyte colony-stimulating factor (G-CSF),alpha-glactosidase A, alpha-L-iduronidase (rhIDU; laronidase), N-acetylgalactosamine-4-sulfatase (rhASB; galsulfase) Tissue plasminogen activator (TPA), Glucocerebrosidase, Interferon (IF) Interferon-beta-1a, Interferon beta-1b, Insulin-like growth factor 1 (IGF-1), somatotropin (ST) and chymosin.

Other examples of exogenous polynucleotides which may be expressed in accordance with the present teachings include, but are not limited to, polypeptides such as peptide hormones, antibodies or antibody fragments (e.g., Fab), enzymes and structural proteins or dsRNA, antisense/ribozyme transcripts which can be directed at specific target sequences (e.g., transcripts of tumor associated genes) to thereby downregulate activity thereof and exert a therapeutic effect. Similarly, protective protein antigens for vaccination (see, for example, Babiuk S et al J Control Release 2000; 66:199-214) and enzymes such as fibrinolysin for treatment of ischemic damage (U.S. Pat. No. 5,078,995 to Hunter et al) may expressed in the cells for transdermal or transcutaneous delivery. The therapeutic protein can also be a prodrug.

Methods of expressing exogenous polynucleotides in cells are well known in the art.

As used herein, the term "expressed" when used in context with the exogenous polynucleotide refers to generation of a polynucleotide (transcript) or a polypeptide product.

An integrative or episomal nucleic acid expression construct may be employed.

Thus, the expression construct can be designed as a gene knock-in construct in which case it will lead to genomic integration of construct sequences, or it can be designed as an episomal expression vector.

In any case, the expression construct can be generated using standard ligation and restriction techniques, which are well known in the art (see Maniatis et al., in: Molecular Cloning: A Laboratory Manual, Cold Spring Harbor Laboratory, New York, 1982). Isolated plasmids, DNA sequences, or synthesized oligonucleotides are cleaved, tailored, and religated in the form desired.

At its minimum, the expression vector of the present invention comprises a polynucleotide encoding the gene of interest.

The expression vector of the present invention may also include additional sequences which render this vector suitable for replication and integration in prokaryotes, eukaryotes, or preferably both (e.g., shuttle vectors) and ultimately in the cells described herein. Typical cloning vectors contain transcription and translation initiation sequences (e.g., promoters, enhancers) and transcription and translation terminators (e.g., polyadenylation signals).

In addition to the elements already described, the expression vector of the present invention may contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Examples of mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Recombinant viral vectors may also be used to transduce (i.e. infect) the cells of the present invention. Viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell.

Retroviral constructs of the present invention may contain retroviral LTRs, packaging signals, and any other sequences that facilitate creation of infectious retroviral vectors. Retroviral LTRs and packaging signals allow the polypeptides of the invention to be packaged into infectious particles and delivered to the cell by viral infection. Methods for making recombinant retroviral vectors are well known in the art (see for example, Brenner et al., PNAS 86:5517-5512 (1989); Xiong et al., Developmental Dynamics 212:181-197 (1998) and references therein; each incorporated herein by reference).

Examples of retroviral sequences useful in the present invention include those derived from adenovirus, lentivirus, Herpes simplex I virus, or adeno-associated virus (AAV). Other viruses known in the art are also useful in the present invention and therefore will be familiar to the ordinarily skilled artisan.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Once the mixture of polymerizing agent, soluble decellularized ECM and cells is obtained, microparticles are generated.

Typical diameters of the microparticles are between 100-1500 μm, more preferably between 300-1000 μm.

According to one embodiment, the mixture is extruded into a crosslinking solution through an aperture to generate microparticles.

As used herein, the term "extruding" as used herein refers to the forcing of a flowable material out through a relatively narrow aperture (i.e. a nozzle in the widest sense), e.g. through a needle.

According to one embodiment the aperture has an inner diameter of about 10-100 gauge (ga) (e.g. about 21 ga).

Typical flow rate of extrusion are about 5-10 ml/min—e.g. 6.7 ml/min. The size of the falling droplets and thus the size of the microparticles generated may be regulated by altering the droplet falling distance. Exemplary droplet falling distances are between 2-5 cm—e.g. 3.5 cm.

Exemplary crosslinking solutions contemplated by the present invention include for example calcium chloride (e.g. 1.5%) or strontium in buffered solutions (e.g. PBS or HBS).

Another way of generating microparticles is by emulsification with paraffin oil. This may be particularly effective when using agarose as the polymerizing agent. To induce gelation of the agarose, the mixture is cooled and the oil phase is removed by suction.

The microparticles are then liquefied by subjecting the microparticles to depolymerizing conditions (e.g. adding a depolymerizing agent). Such conditions allow the polymerizing agent to dissolve and diffuse from the particles.

The precise method selected for depolymerizing the polymerizing agent will depend of the polymerizing agent used.

Examples of depolymerizing agents useful for depolymerizing alginate include sodium citrate (1.5%), HEPES and EDTA. The contacting time for the depolymerizing agent is typically between 1 minute and one hour—e.g. five minutes.

Chitosan may be dissolved by lowering the pH to about 6.

The present invention further contemplates coating the microspheres with a polyion prior to the depolymerizing step and following the crosslinking step.

Preferably, the polyion is selected from the group consisting of poly-L-lysine, poly-D-lysine, poly-L,D-lysine, polyethylenimine, polyallylamine, poly-L-ornithine, poly-D-ornithine, poly-L,D-ornithine, polyL-aspartic acid, poly-D-aspartic acid, poly-L,D-aspartic acid, polyacrylic acid, poly-L-glutamic acid, poly-D-glutamic acid, poly-L,D-glutamic acid, succinylated poly-L-lysine, succinylated poly-D-lysine, succinylated poly-L,D lysine, chitosan, polyacrylamide, poly(vinyl alcohol) and combinations thereof. More preferably, the polyion is a polycation selected from the group consisting of poly-L-lysine, poly-D-lysine, poly-L,D-lysine, poly-L-ornithine, poly-D-ornithine, poly-L,D ornithine, chitosan, polyacrylamide, poly(vinyl alcohol), and combinations thereof. Most preferably, the polyion is poly-L-lysine.

According to another embodiment, the polyion is chitosan.

Using the methods described herein, microparticles are obtained with novel characteristics.

Thus, according to another aspect of the present invention there is provided a microparticle for cell encapsulation, having a core which comprises continuous fibers of decellularized extracellular matrix (ECM).

The term "microparticle" refers to a particle being of micron dimensions. The microparticles may be of any shape, including, without limitation, elongated particle shapes, such as nanowires, or irregular shapes, in addition to more regular shapes, such as generally spherical, hexagonal and cubic microparticles. According to one embodiment, the microparticles are generally spherical.

Rounded particles are typically characterized quantitatively by a geometrical quantity known as sphericity, which generally quantifies the deviation of a particular geometrical shape from a perfect sphere.

Ideally, the sphericity of a three dimensional object is calculated by dividing the volume of the object to the volume of a sphere circumscribing the object. However, for some objects, the determination of the volume is difficult and oftentimes impossible. Therefore, for practical reasons, an alternative "two-dimensional" definition of sphericity is used. According to this alternative, the sphericity is defined as the ratio between the area of the projection of the object onto a certain reference plane and the area of a circle circumscribing the projection. For example, suppose that an image of the object is displayed on a planar display, then the planar display can be considered as a reference plane and the image of the object can be considered as the projection of the object on the reference plane.

Thus, denoting the area of the image by A and the perimeter of the image by P, the sphericity, s, can be defined as $s=4\pi cA/P^2$. As will be appreciated by one of ordinary skill in the art, when the image is a perfect circle, $A=\pi(P/2\pi)^2=P^2/4\pi$ and $s=1$. When the area of the image is 0 (i.e., the image is a line or a curve) $s=0$.

Unless otherwise defined, "sphericity," as used herein, refers to two-dimensional sphericity.

It is recognized that the "two dimensional" sphericity is, to a good approximation, equivalent to the "three dimensional" sphericity (ratio of volumes), provided it is calculated and averaged over many particles (say 10 or more) or many different reference planes. In such event, starting from the "two dimensional" sphericity, s, the "three dimensional" sphericity can be defined as the cubic root of $s^2$.

According to a preferred embodiment of the present invention the sphericity of the particle is at least 80% more preferably at least 85%.

The microparticles generated according to the method of the present invention are substantially homogeneous, i.e. are all of a uniform shape and size. According to one embodiment the microparticle population does not comprise microparticles which differ by more than 5%, 10%, 20% or 30% from the size of the average microparticle in the population.

As used herein, the phrase "a core which comprises continuous fibers of decellularized ECM" refers to a core wherein the ECM fibers are distributed homogenously throughout the core and are not present as clusters or particles.

According to one embodiment, the core is essentially devoid of polymerizing agent (e.g. alginate).

The microparticles may comprise an outer layer encapsulating the inner core. Such a layer may be fabricated from a polyion, as further described herein above. Typically, an amount of polymerizing agent in outer layer is at least 10 times, at least 20 times, at least 50 times, at least 100 times the amount of polymerizing agent in the core. The thickness of the outer layer is typically between 5 μm to 50 μm—e.g. between 10 μm to 30 μm.

The microparticles may be stored at temperatures above 25° C. (e.g. about 37° C.) in order to enhance the solidification of the particles are aid in maintenance of the structural integrity of the microparticles.

Encapsulated cells generated according to the present teachings can be used in a myriad of research and clinical applications.

Thus, according to another aspect of the present invention there is provided a method of transplanting encapsulated cells such as for treating a medical condition (e.g., pathology, disease, syndrome) which may benefit from cell transplantation in a subject in need thereof.

As used herein the term "treating" refers to inhibiting or arresting the development of a pathology and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology. Preferably, the term "treating" refers to alleviating or diminishing a symptom associated with a cancerous disease. Preferably, treating cures, e.g., substantially eliminates, the symptoms associated with the medical condition.

As used herein "a medical condition which may benefit from cell transplantation" refers to any medical condition which may be alleviated by administration of the encapsulated cells of the present invention.

Examples of such medical conditions include, but are not limited to, stem cell deficiency, heart disease, neurodegenerative diseases, glaucoma neuropathy, Parkinson's disease, cancer, Schizophrenia, Alzheimer's disease, stroke, burns, loss of tissue, loss of blood, anemia, autoimmune disorders, diabetes, arthritis, graft vs. host disease (GvHD), neurodegenerative disorders, chronic pain, autoimmune encephalomyelitis (EAE), systemic lupus erythematosus (SLE), rheumatoid arthritis, systemic sclerosis, Sjorgen's syndrome, multiple sclerosis (MS), Myasthenia Gravis (MG), Guillain-Barrè Syndrome (GBS), Hashimoto's Thyroiditis (HT), Graves's Disease, Insulin Dependent Diabetes Melitus (IDDM) and Inflammatory Bowel Disease.

The term or phrase "transplantation", "cell replacement", "implantation" or "grafting" are used interchangeably herein and refer to the introduction of the cells of the present invention to target tissue.

As used herein the term "subject" refers to any subject (e.g., mammal), preferably a human subject.

In any of the methods described herein, the cells or media can be administered either per se or, preferably as a part of a pharmaceutical composition that further comprises a pharmaceutically acceptable carrier.

As used herein a "pharmaceutical composition" refers to a preparation of one or more of the chemical conjugates described herein, with other chemical components such as pharmaceutically suitable carriers and excipients. The purpose of a pharmaceutical composition is to facilitate administration of a compound to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

According to a preferred embodiment of the present invention, the pharmaceutical carrier is an aqueous solution of saline.

Techniques for formulation and administration of drugs may be found in "Remington's Pharmaceutical Sciences," Mack Publishing Co., Easton, Pa., latest edition, which is incorporated herein by reference.

One may administer the pharmaceutical composition in a systemic manner (as detailed hereinabove). Alternatively, one may administer the pharmaceutical composition locally, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For any preparation used in the methods of the invention, the therapeutically effective amount or dose can be estimated initially from in vitro and cell culture assays. Preferably, a dose is formulated in an animal model to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals.

The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition, (see e.g., Fingl, et al., 1975, in "The Pharmacological Basis of Therapeutics", Ch. 1 p. 1). For example, Parkinson's patient can be monitored symptomatically for improved motor functions indicating positive response to treatment.

For injection, the active ingredients of the pharmaceutical composition may be formulated in aqueous solutions, preferably in physiologically compatible buffers such as Hank's solution, Ringer's solution, or physiological salt buffer.

Dosage amount and interval may be adjusted individually to levels of the active ingredient which are sufficient to effectively regulate the neurotransmitter synthesis by the implanted cells. Dosages necessary to achieve the desired effect will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the individual being treated, the severity of the affliction, the manner of administration, the judgment of the prescribing physician, etc. The dosage and timing of administration will be responsive to a careful and continuous monitoring of the individual changing condition. For example, a treated Parkinson's patient will be administered with an amount of cells which is sufficient to alleviate the symptoms of the disease.

Depending on the medical condition, the subject may be administered with additional chemical drugs (e.g., immunomodulatory, chemotherapy etc.) or cells.

Preferably the HSCs and stromal cells share some common HLA antigens.

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods

Figure 1:
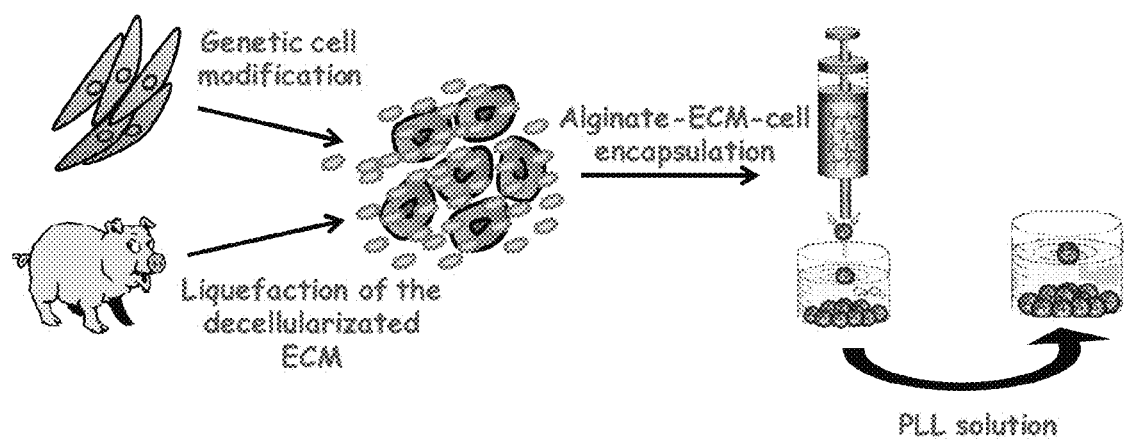

Cells are mixed with soluble decellularized ECM (e.g. extracted from porcine or sheep organs) together with a polymer or hydrogel—e.g. alginate (FIG. 1).

Once the alginate-ECM-cells capsules are made, the capsules may be coated with poly-1-lysine (PLL) or chitosan. The coated microcapsules alginate core is then liquefied using an additional step of suspension in HEPES sodium citrate solution (or EDTA or other chelating agents). The citrate solution chelates calcium and dissolves the alginate inside the capsule. The coating polymer network connects the alginate only (width of coat range from 10 µm to 30 µm) at the microcapsules periphery and reduces the osmotic pressure inside the capsule. (Coated polymer can also be connected to negative components of the ECM at the microcapsules periphery, in case of using positive charged polymer for the microcapsule preparation such as chitosan).

Figure 2:
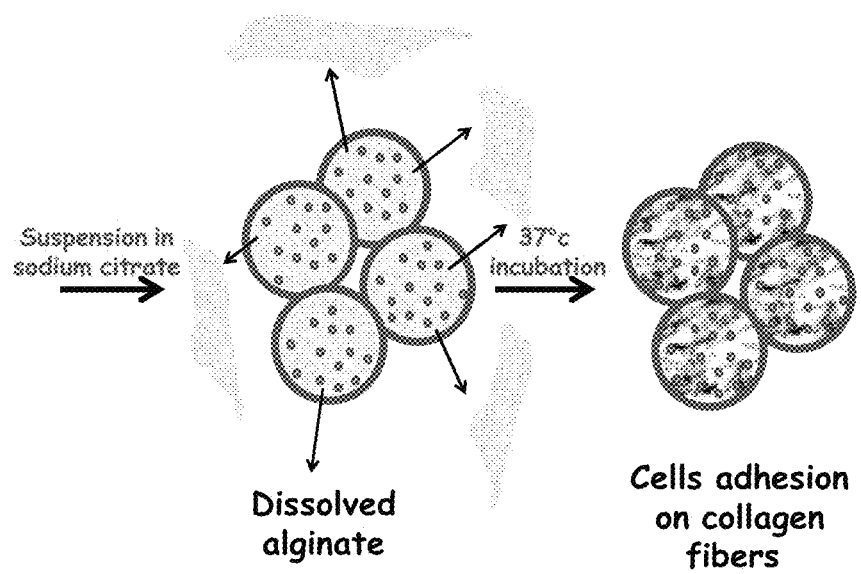

In that way the present inventors obtained a capsule fabricated entirely from ECM and coated with a coating polymer such as PLL or chitosan. At 37° C. incubation, the ECM solidifies to generate a network of collage fibers inside the capsules while cells are attached or dispersed therein (alginate to ECM ratio range from 1%:99% to less than 0.1% of alginate) (FIG. 2).

Preparation of Soluble Decellularized ECM: Polymer/Hydrogel-ECM-cell encapsulation are prepared from desirable cells and native decellularized ECM. Native tissue is washed in PBS to remove all residual blood. The tissue is sliced and incubated in hyper-hypo-tonic solutions of NaCl. Slices are then incubated with trypsin-EDTA 0.05% for 24 hrs (this was repeated twice). For chemical removal, tissue is then washed several times with triton X-100+ammonium hydroxide solutions and finally several washing cycles of 48 hrs with PBS until no residue of foam is obtained. ECM is sterilized by washing for two hours with ethanol (70%) and following two washes with double distilled water. Lyophilized ECM and protease enzyme (e.g. pepsin or/and collagenase or/and trypsin) at different concentration and biological activities are mixed in 15 ml of 0.05 M to 0.2M HCl and kept at a constant stirring for 48 h at room temperature (25° C.). The resultant viscous solution of digested ECM solution has a pH of approximately 3.0-4.0. The activity of the enzyme is irreversibly inactivated according to the type of enzyme—for example for pepsin the pH will be raised to 7.4. The solubilized matrix still retains ECM proteins and peptide fragments therefore, the matrix retains its biochemical components, as is necessary for cell-matrix interactions. ECM are considered completely solubilized, when no particles are detected in solution.

Basic protocol for the Preparation of Hydrogel-ECM-cell Encapsulation: Solubilized ECM is used for cell encapsulation with alginate. Alginate (medium or low viscosity, with different G content and concentrations (NOVA MATRIX, Norway)) is mixed with solubilized ECM and cells are added. Hydrogel-ECM-cell mixture is infused at a constant flow rate of 6.7 ml/min through a 21 Gauge needle. Constant airflow of 1 psi is used for intersection of the mixture into droplets. Droplets of a falling distance of 3.5 cm is necessary to create the desired size microcapsules. The hydrogel was then cross-linked with a crosslinker such as $CaCl_2$ 1.5% or strontium solutions for alginate. Coating the hydrogel spheres with PLL or chitosan or other coating polymers creates the desirable semi permeable microcapsules. The capsules are then liquefied using Na-citrate 1.5% solution for 5 minutes or EDTA in order to get an ECM only based capsule surrounded by coated polymer.

Example 2

Alginate-poly-1-lysine (PLL) microcapsules were prepared with human liver cells (Hum Hep) and human mesenchymal stem cells (hMSC). Prior to encapsulation, cells were genetically modified to express the PDX-1 gene, which is a pancreatic transcription factor that regulates the expression of multiple genes in beta cells including those that encode insulin. PDX-1 induces trans-differentiation of cells into cells that secret insulin in a glucose regulated manner. Microcapsules were analyzed for size, morphology, cell viability and distribution within the capsules.

Results

Figure 3A:
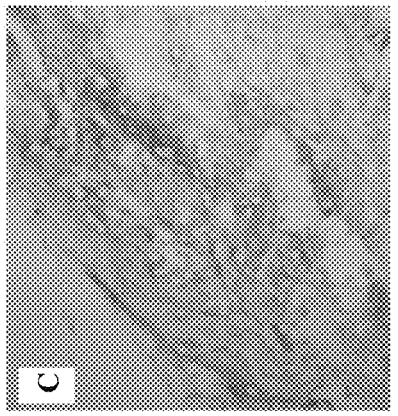
Figure 3B:
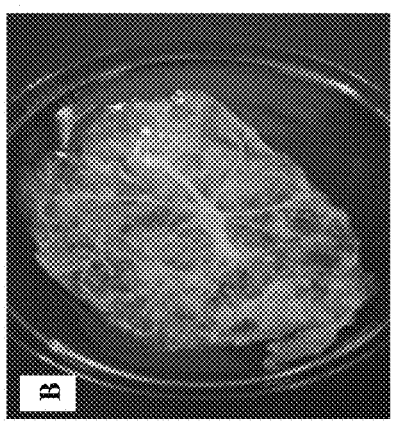
Figure 3C:
Figure 3D:
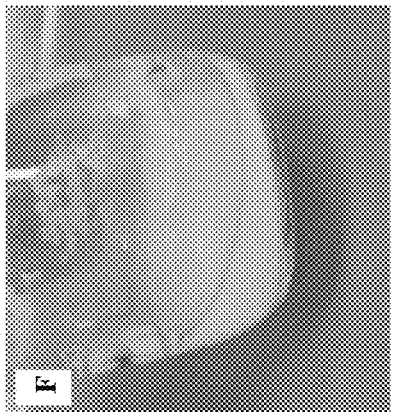
Figure 3E:
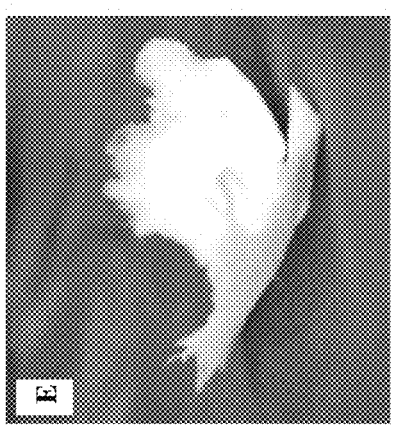
Figure 3F:
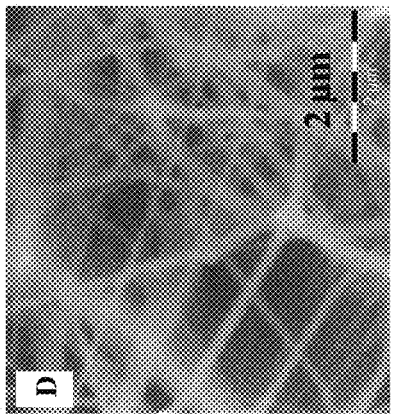

Acellular pancreatic ECM was generated. Histological analysis revealed complete cell removal while maintaining the ECM fibers architecture as apparent in SEM imaging (FIG. 3D). After decellularization, the ECM was lyophilized and liquefied, using proteolytic enzymes, as illustrated in FIGS. 3E-F. Proteomic analysis revealed the preservation of major ECM components in both decellularized and liquefied ECM (FIG. 4A). Both the storage modulus (G') and the loss modulus (G") changed over time and were characterized after the temperature of the sample was raised from 4° C. to 37° C. (FIG. 4B). G' and G" reached steady state after approximately 4-5 minutes suggesting that gelation had occurred.

Figure 5J:
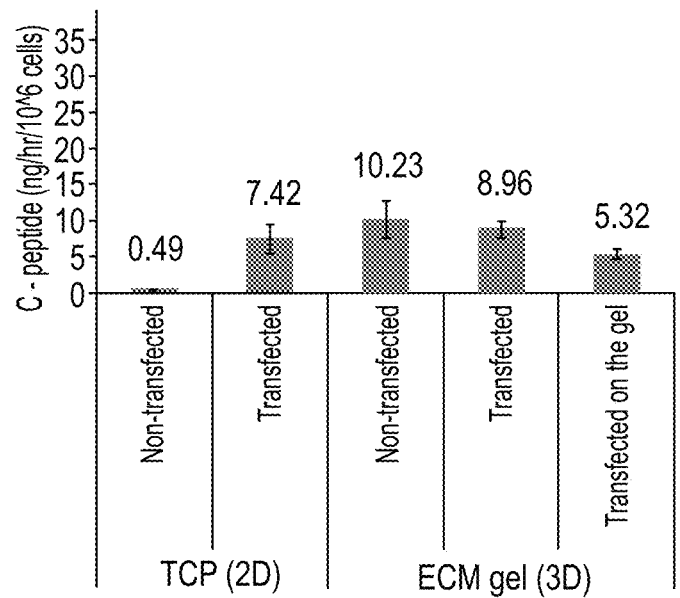
Figure 5K:
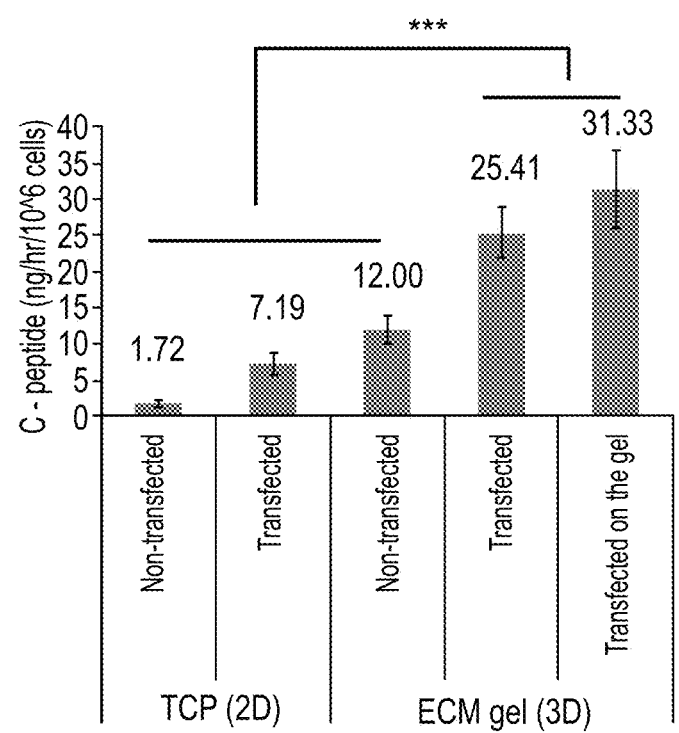

Prior to the preparation of encapsulated ECM-cells, the biological activity of insulin producing cells seeded on ECM gels was evaluated as compared to those seeded on a plate. A thin layer of liquefied ECM was spread in a 6-wells plate (FIG. 5A). Gels, made from the liquefied ECM which were incubated at 37° C., exhibited a 3D fiber network structure similar to the native tissue (FIGS. 5B-C) with a pore size and cell-fiber interaction suitable for supporting cellular proliferation (FIGS. 5D-G). Moreover, in comparison to cells seeded on a plate (FIG. 5H), cells seeded on the gel exhibited a more elongated shape, probably due to the formation of focal adhesions which connect the ECM fibers to actin filaments of the cells (FIG. 5I). The efficiency of cell seeding was assessed by IN Cell 2000, which imaged and analyzed cell viability over time by analyzing Hoechst staining. C-peptide secretion of PDX-1 transduced cells or non-transduced cells was evaluated. Within the pancreatic β-cell, proinsulin is cleaved into one molecule of C-peptide and one molecule of insulin. C-peptide is subsequently released into the circulation at concentrations equimolar to those of insulin. In contrast to insulin, C-peptide is minimally extracted by the liver. Therefore, peripheral C-peptide concentration reflects the secretion of β-cell more accurately than insulin. As seen in FIG. 5J, the 3D culture on the gel did not affect insulin production of transfected hMSC. However, gel 3D culture did significantly increase the insulin production of Hum Hep cells as compared to cells seeded on a plate (FIG. 5K). Thus, it can be deduced that the enclosed ECM components on 3D gels attract Hum Hep cells and contribute to insulin production.

The liquefied ECM was then incorporated with transfected liver cells or hMSCs. The solubilized ECM and cells were mixed with alginate and co-extruded through calcium and PLL solutions to produce Alginate-PLL capsules containing both insulin producing cells and acellular pancreatic ECM.

As illustrated in FIGS. 6A-D, encapsulated cells were viable for more than 120 days using the Alamar Blue assay and more than 108 days using the Fluorescein Diacetate (FDA) cell viability assay.

Figure 7A:
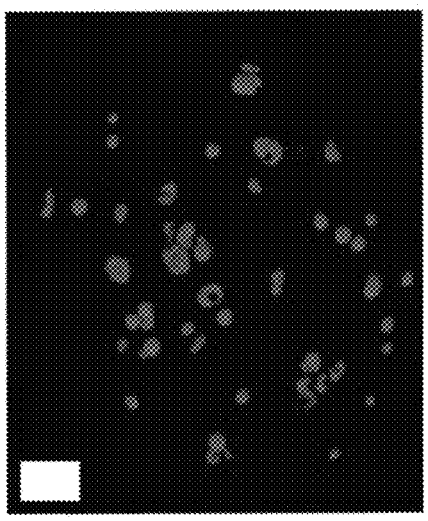
Figure 7B:
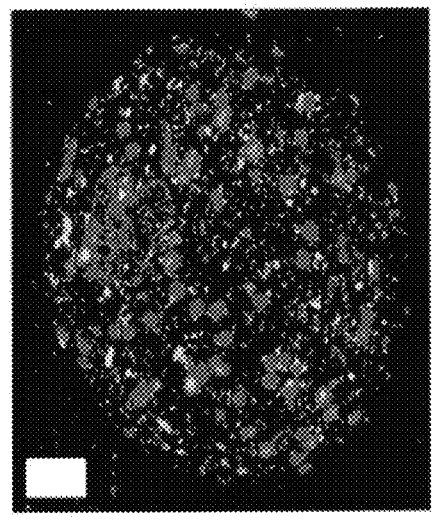
Figure 7C:
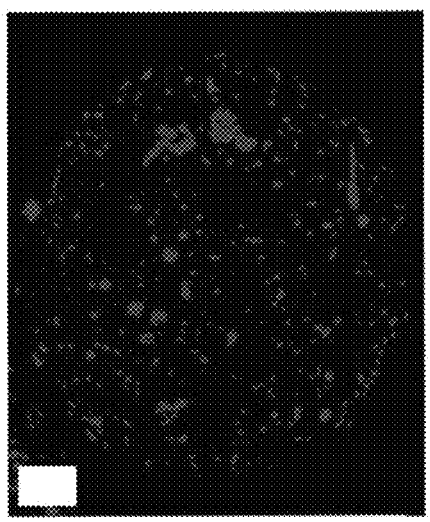
Figure 7D:
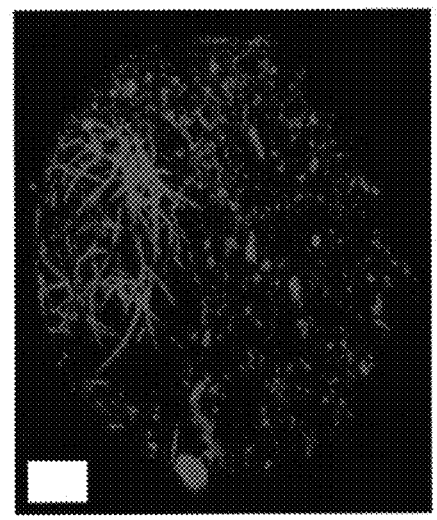
Figures 7E, 7F, 7G:
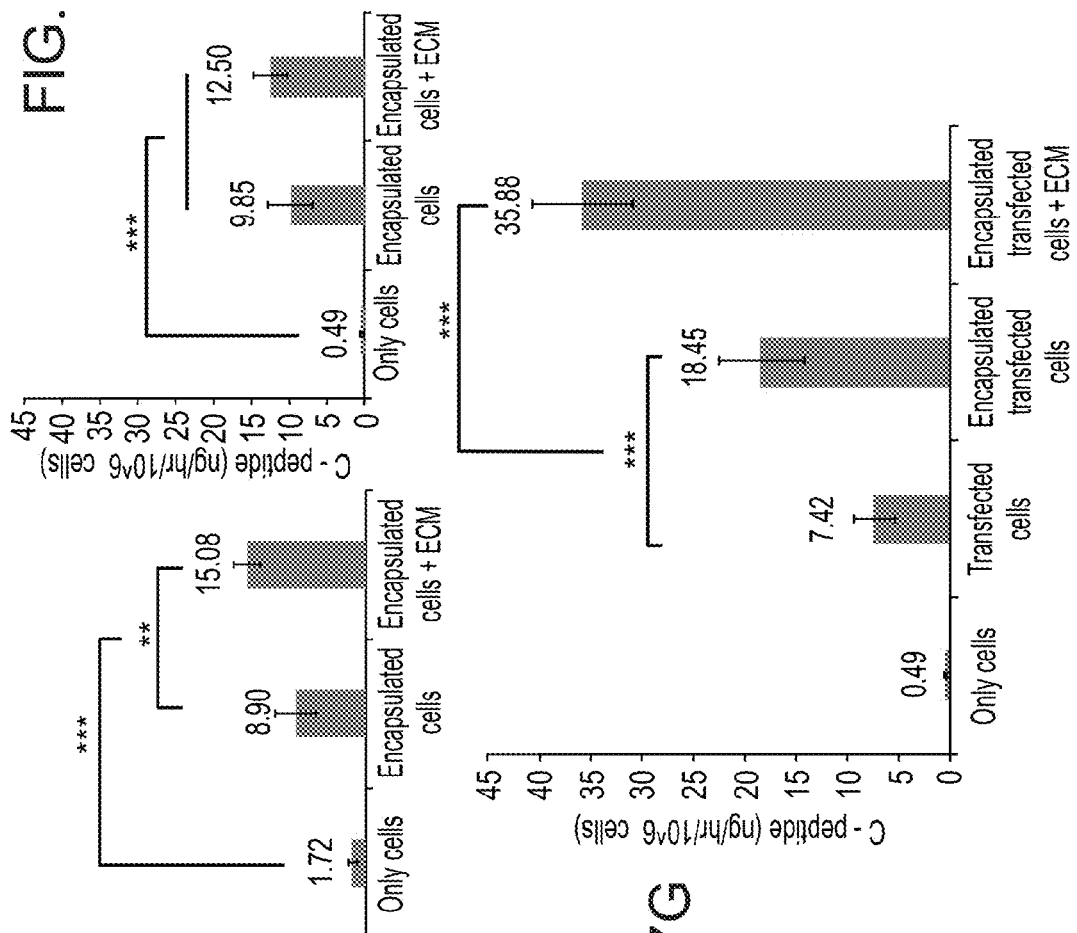

Therapeutic efficacy of encapsulated Hum Hep cells and hMSC secreting insulin was performed. In the microparticles, collagen fibers were seen to self-assemble into typical 3D fibrous structures inside the capsule (FIG. 7C). Moreover, cell clusters were noted to organize around large collagen depositions originating from the liquefied ECM (FIGS. 7A, B and D). Cell encapsulation did not affect the insulin production of transfected liver cells, although it did increase the insulin production of encapsulated non-transfected cells (FIG. 7E). The results support the present hypothesis that the microenvironment inside the capsule permits a native environment that encourages the bioactivity of these cells as glucose dependent cells even without viral transfection. However, the insulin production of hMSCs, both transfected and untransfected, was significantly affected by ECM-cell encapsulation (FIGS. 7F-G). These results indicate that the ECM-microenvironment within the microcapsule is not only permissive for hMSC transdifferentiation into β-cells, but actually contributes to insulin secretion.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A microparticle which encapsulates a plurality of cells, having a core which comprises a polymerizing agent and decellularized extracellular matrix (ECM) of a tissue, said decellularized ECM comprising: continuous fibers of collagen, cell adhesion polypeptides and space-filling molecules of the tissue, said decellularized ECM retaining structural properties of the ECM of said tissue; and an outer layer which comprises the same polymerizing agent as said core, wherein an amount of said polymerizing agent in said outer layer is at least 10 times the amount of said polymerizing agent in said core.

2. The microparticle of claim 1, wherein said outer layer further comprises a polyion.

3. The microparticle of claim 2, wherein the polyion is selected from the group consisting of poly-L-lysine, poly-D-lysine, poly-L,D-lysine, poly-L-ornithine, poly-D-ornithine, poly-L,D ornithine, chitosan, polyacrylamide, poly(vinyl alcohol) and combinations thereof.

4. The microparticle of claim 1, wherein said polymerizing agent is selected from the group consisting of chitosan, polymethacrylic acid, a polysaccharide, poly (ethylene glycol) (PEG) and poly (hydroxyethyl) methacrylate (HEMA).

5. The microparticle of claim 4, wherein said polysaccharide is selected from the group consisting of alginate, hyaluronic acid and agarose.

6. The microparticle of claim 1, wherein a thickness of said outer layer is between about 10 μm to 30 μm.

7. The microparticle of claim 1, being between 300-1000 μm in diameter.

8. The microparticle of claim 1, wherein said decellularized extracellular matrix is derived from pancreatic tissue.

9. The microparticle of claim 1, wherein said decellularized extracellular matrix is derived from cardiac tissue.

10. The microparticle of claim 8, further comprising cells which express pancreatic beta cell markers.

11. The microparticle of claim 9, further comprising cells which express cardiac markers.

12. A pharmaceutical composition comprising the microparticle of claim 1 as the active agent and a pharmaceutically acceptable carrier.

13. The microparticle of claim 1, wherein said continuous fibers of collagen are distributed homogenously throughout the core and are not present as clusters or particles.

14. The microparticle of claim 1 being generated by:
a) decellularizing ECM of a tissue under conditions that the decellularized ECM retains a structural property of said ECM of said tissue;
b) contacting solubilized decellularized ECM and cells in the presence of a polymerizing agent to generate a mixture;
(c) generating microparticles comprising said cells; and
(d) depolymerization said polymerizing agent.

* * * * *